(12) United States Patent
Schneider et al.

(10) Patent No.: US 6,306,457 B1
(45) Date of Patent: Oct. 23, 2001

(54) COATED SYSTEM AND METHOD FOR ITS MANUFACTURE AND ITS USE

(75) Inventors: Jens Stefan Schneider, Anderson, SC (US); Frank Stanglmeier, Moeglingen; Bernd Schumann, Rutesheim, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/360,047

(22) Filed: Jul. 23, 1999

(30) Foreign Application Priority Data

Jul. 23, 1998 (DE) .............................. 198 33 081

(51) Int. Cl.[7] .......................... B32B 15/04; G01N 27/406
(52) U.S. Cl. ...................... 427/125; 427/304; 427/305; 427/430.1; 204/429; 205/170; 205/183
(58) Field of Search ....................... 204/429, 424–428; 205/170, 183, 162, 163, 161; 427/58, 125, 304, 305, 430.1, 435–438

(56) References Cited

U.S. PATENT DOCUMENTS

| | | | |
|---|---|---|---|
| 4,021,326 | * 5/1977 | Pollner et al. .................... | 204/429 |
| 4,097,353 | * 6/1978 | Kishida et al. .................... | 204/429 |
| 4,199,425 | 4/1980 | Sinkevitch ...................... | 204/429 |
| 4,541,905 | * 9/1985 | Kuwana et al. .................... | 205/112 |
| 4,863,583 | * 9/1989 | Kurachi et al. .................... | 204/424 |
| 5,006,221 | * 4/1991 | Uchikawa et al. ................. | 204/426 |
| 5,080,689 | * 1/1992 | Pal et al. ....................... | 427/115 |
| 5,326,597 | * 7/1994 | Sawada et al. .................... | 427/448 |

FOREIGN PATENT DOCUMENTS 2198750   6/1988   (GB) .

\* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

A coating system and a method for its manufacture are provided. An electrically conductive base coat and a porous overcoat lying over the base coat are arranged on a ceramic substrate. At least one additional deposited layer is arranged on the base coat in such a way that the additional layer is formed in the pores of the porous overcoat adjacent to the base coat. The additional layer is deposited either by currentless or electrolytic deposition. For electrolytic deposition of the additional layer, the ceramic substrate sintered with the base coat and the overcoat is submerged in an electrolytic bath and the base coat is connected as a cathode. The currentless deposition takes place from a solution of the metal to be deposited with the addition of a reducing agent.

14 Claims, 2 Drawing Sheets

COATED SYSTEM AND METHOD FOR ITS MANUFACTURE AND ITS USE

FIELD OF THE INVENTION

The present invention relates to a coating system, and a method for the manufacture and use of the coating system

BACKGROUND INFORMATION

Conventional coating systems can be found, for example, in electrochemical oxygen sensors in which a ceramic body produced from a solid electrolyte is provided with at least one electrode exposed to a gas to be analyzed, and a porous overcoat covering the electrode. The electrode is made up of a catalytically active material such as platinum which is capable of adjusting the equilibrium setting of the gas to be analyzed on the electrode surface.

U.S. Pat. No. 4,199,425 describes a sensor in which an additional catalytic material, rhodium, is introduced into the pores of the porous overcoat by impregnation and subsequent calcination. The rhodium precipitates onto the pore walls of the entire overcoat in the form of ultra-fine particles so that no specific coating thickness can be set in the porous overcoat.

A method for the currentless deposition of metals onto metallic surfaces and the monitoring of these processes is described in British Patent No. 2 198 750. However, this method does not make the specific application of a metallic coating onto an electrode surface through a porous protective coating possible.

SUMMARY

An advantage of the coating system according to the present invention is that one or more additional layers having a defined layer thickness are formed on an electrically conductive base coat. Another advantage is that the additional layer or layers arranged immediately adjacent to the electrically conductive base coat does not or do not completely fill up the pores of the porous overcoat. This preserves the protective effect of the porous overcoat as well as an adequate gas transfer through the overcoat. The method according to the present invention makes it possible to deposit the additional layers onto the base coat through the porous overcoat after the ceramic body has already been sintered. As a result, materials can be used for the additional layers that otherwise would not stand up to the high sintering temperature.

The subsequent electrolytic or currentless deposition of at least one layer on the base coat makes it possible to modify the functional properties of the base coat. This is particularly advantageous for the modification of the functional properties of an electrode in gas sensors with regard to their specific gas selectivity and/or control layer.

A particularly marked influence of the materials of the base coat and the additional layer on each other is achieved by a thermal aftertreatment of the coating system after the additional layer has been deposited. For example, a temperature range of 1200° C.±100° C. has proven to be favorable for an Au/Pt coating system. At this temperature, the metal atoms of the additional layer diffuse into the metal of the adjacent base coat. Such a mixing phase of the materials is necessary, for example, for electrodes of gas sensors intended to respond to a specific gas species. For example, in order to form an HC-selective or $NO_x$-selective sensor, the electrode of a gas sensor can be modified in such a way that the electrode then has a special affinity for hydrocarbons or nitrogen oxides. It is further possible to adjust the catalytic properties and the thermal properties of the gas sensor by the selection of the material for the additional layer. Moreover, the control layer of the sensor can be influenced by the selection of the material and/or the thickness of the deposited layer.

An advantage of an currentless deposition of an additional layer onto a base coat in relation to electrolytic deposition is that only electrically contacted compartments of the base coat are coated in electrolytic deposition whereas all the particles on the surface of the base coat are coated in currentless deposition. This is advantageous since parts of the base coat that are electrically insulated at room temperature can definitely be contacted at the very high operating temperatures of a gas sensor via the solid electrolyte substrate which is then conductive. Thus, when the coating system is used as a measuring electrode and these parts are not coated, they have an unfavorable influence on the resulting sensor signal.

A further advantage is that a cermet layer is used as the electrically conductive base coat, the cermet layer forming a solid connection with the ceramic substrate during sintering of the ceramic body due to the ceramic component of the cermet layer.

DETAILED DESCRIPTION

Figure 1:
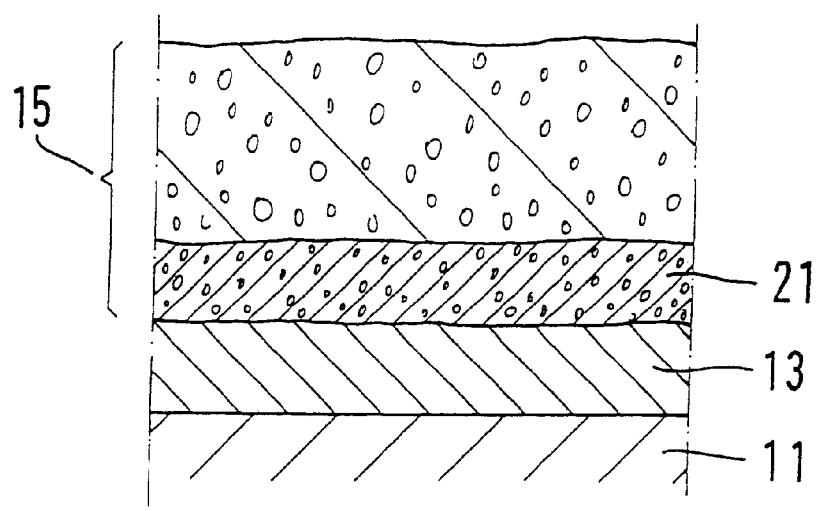
FIG. 1 shows a sectional representation of a first exemplary embodiment of a coating system according to the present invention.
Figure 2:
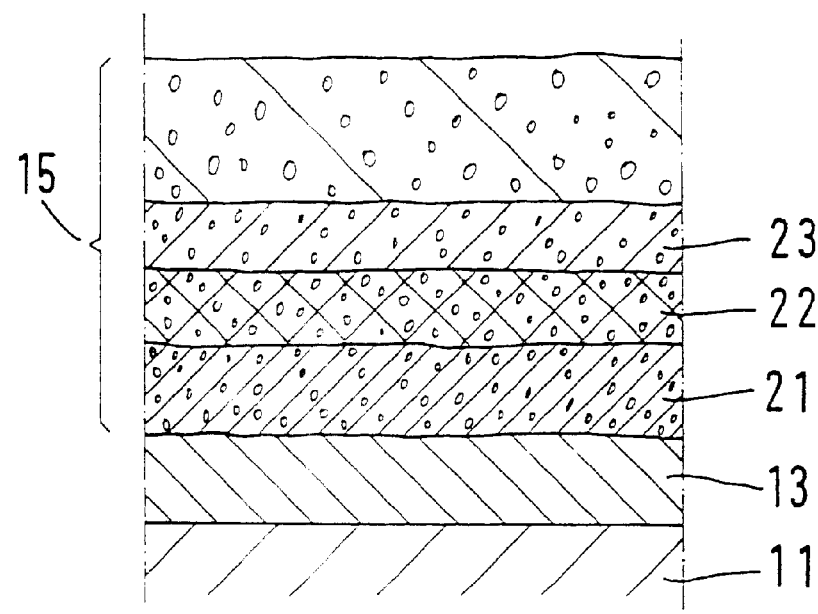
FIG. 2 shows a sectional representation of a second exemplary embodiment of the coating system according to the present invention.

The coating system of the present invention has, for example, the layer structure shown in FIG. 1 or 2. According to the coating system in FIG. 1, an electrically conductive base coat 13 made up of a Pt-cermet and having an electrical terminal contact 35 is arranged on a ceramic substrate 11 made up of a solid electrolyte such as $ZrO_2$. A porous overcoat 15 is arranged on base coat 13. Adjacent to base coat 13, an additional layer 21 is formed on the base coat in the pores of overcoat 15. Layer 21 is thus in direct contact with base coat 13.

FIG. 2 shows a second exemplary embodiment of a coating system. In this case, layer 21 is formed in the pores of overcoat 15 over base coat 13 and a second layer 22 is formed over layer 21 and a third layer 23 is formed over layer 22. Layer 21 is of gold, layer 22 of rhodium or iridium and layer 23 is of nickel or chromium. This embodiment shows that even a complex, multilayer coating structure can be implemented in a simple manner. As a mixed potential electrode, such a coating system is used in mixed potential sensors. Mixed potential electrodes are electrodes which are not able or not completely able to catalyze the equilibrium setting of a gas mixture on their surface. If a mixed potential electrode is connected together with a reference electrode of platinum, such an arrangement then forms a mixed potential sensor. An appropriate selection of material for additional layer 21 makes it possible to set the selectivity of the resulting electrode specifically for one gas species and/or to specifically modify the control layer of the sensor. Thus, for example, the low temperature characteristics of an oxygen sensor can be improved by a rhodium layer on a Pt electrode. With a layer structure shown in FIG. 2 and via an appropriate selection of materials for layers 21, 22, 23, it is also possible to specifically modify the catalytic properties of the electrode surface in addition to setting the selectivity.

To manufacture the coating system according to FIG. 1, ceramic substrate 11 provided with electrically conductive base coat 13 and porous overcoat 15 is sintered at a temperature of 1400° C. However, it is also possible to apply overcoat 15 to base coat 13 only after sintering. Not only $ZrO_2$, but also $Al_2O_3$ is suitable as ceramic substrate 11.

Figure 3:
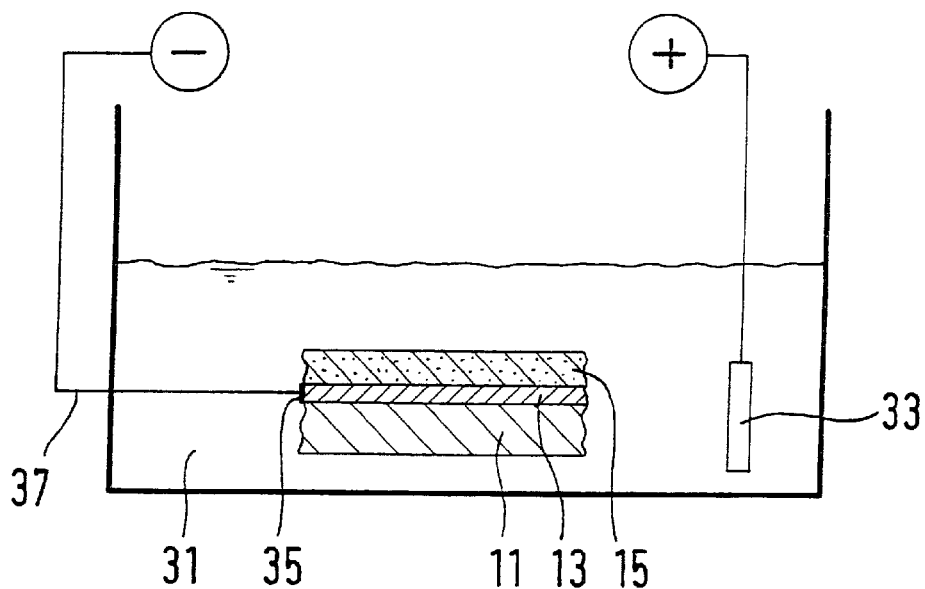
FIG. 3 shows a system to implement the method according to the present invention.
Figure 4:
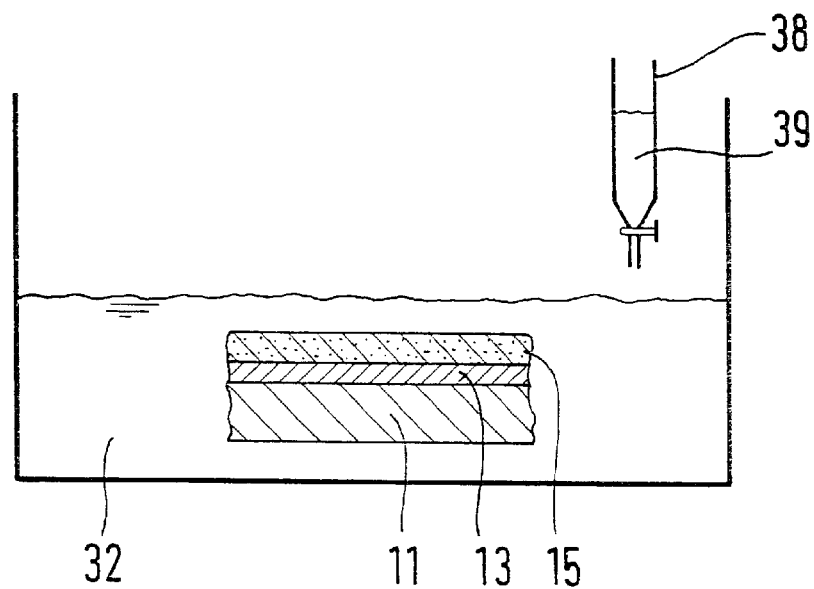
FIG. 4 shows another system to implement the method according to the present invention.

In the present exemplary embodiments, ceramic substrate 11 is provided with a layer 21 according to FIG. 1 and with more than one layer 21, 22, 23 according to FIG. 2, layer 21 or layers 21, 22, 23 being formed in the pores of porous overcoat 15 in superimposed strata. Two examples of how the layers 21, 22, 23 can be formed are illustrated in FIGS. 3 and 4.

A first example is to produce additional layers 21, 22, 23 by electrolytic deposition. A structure based on this method is shown in FIG. 3.

For this purpose, ceramic substrate 11 is placed into an electrolytic bath 31; base coat 13 is electrically contacted at terminal contact 35 and connected as cathode 37. An electrode made of a metal corresponding to the metal of the particular layer 21, 22, 23 to be deposited is used as anode 33 (electrolytic process with sacrificial anode). Water-soluble salts of the metals in question, such as $HAuCl_4$, $IrCl_3 \times H_2O$ or $RhCl_3 \times H_2O$, serve as the electrolyte.

In order to manufacture a sensor to detect hydrocarbons, a coating system according to FIG. 1 is selected, a gold layer being electrolytically deposited as additional layer 21 onto base coat 13 of Pt-cermet. For this purpose, the sintered ceramic body of the sensor is placed into electrolytic bath 31 with an $HAuCl_4$ electrolyte and a gold anode is used as anode 33. At a current intensity of 0.5 to 2 mA and a current duration of 15 to 50 minutes, layer 21 of gold is deposited onto the Pt-cermet base coat 13 at a layer thickness of 1–5 $\mu$m. Layer 21 is formed in the pores of overcoat 15. After deposition of layer 21, the ceramic body is subjected to a tempering at a temperature of 1200° C. During the tempering, an alloy forms between the platinum of base coat 13 and the gold of layer 21, the alloy being namely a platinum-rich gold phase and a gold-rich platinum phase. As a result, the catalytic activity of the platinum of base coat 13 is modified and a mixed potential electrode is formed.

Depending on the area of application, electrolytically produced layer 21 may be made from a noble metal (such as gold, rhodium, iridium), a semi-noble metal (such as palladium, silver), a base metal (such as copper, bismuth, nickel, chromium) or a mixture of these metals.

A coating system according to FIG. 2 may also be produced electrolytically, the corresponding anode materials and/or the corresponding electrolytic baths being used successively in the electrolytic deposition.

Additional layers 21, 22, 23 may also be produced by currentless deposition. An apparatus based on this method is shown in FIG. 4. For this purpose, ceramic substrate 11 with base coat 13 and porous protective coating 15 is submerged in a metallic salt solution or in a solution of a suitable metal complex 32 of the metal to be deposited. After the addition of a chemical reducing agent 39 via a metering device 38, the corresponding metal is deposited with a time delay depending on the nature of the solution. In the process, the added reducing agent produces nascent hydrogen in a first step on the surface of metallic base coat 13, the nascent hydrogen for its part being capable of reducing the metallic salts or metal complexes contained in the solution to elementary metal which then precipitates. An advantage of a direct participation of the electrode surface in the deposition process can primarily be seen in the fact that the metal precipitates in direct contact with base coat 13 and not in the pores of the entire porous protective coating 15.

In order to manufacture a mixed potential sensor, a coating system according to FIG. 1 is used, an additional layer 21 of gold being deposited by currentless deposition on base coat 13 made from a platinum cermet. For this purpose, a ceramic substrate of $ZrO_2$, to which base coat 13 of a platinum cermet is applied and which is covered by a porous protective coating 15, is submerged in a solution 32 of 5 g $HAuCl_4$, in 250 ml water and 50 ml of a 37% formaldehyde solution is added via metering device 38. The solution is heated to 60 to 80° C. with the aid of a heating unit (not shown). The progress of the gold deposition can be readily followed via the discoloration of metallic salt solution 32. After deposition is completed, ceramic substrate 11 is removed from the metallic salt solution and a rinsing and drying treatment takes place. If the coating system is subsequently tempered at a temperature of 1200° C., an alloy is formed between the platinum of base coat 13 and the deposited gold of layer 21. Owing to the lack of catalytic activity, the resulting coating system is suitable as a mixed potential electrode of a mixed potential sensor.

Au, Ni, Co, Cu, Ag, Sn or W may be used as additional metals that are particularly suited for currentless deposition. Primarily aldehydes such as formaldehyde, hydrazine and alcohols are suitable as reducing agent 39.

In order to achieve a complete penetration of porous protective coating 15 with the corresponding metallic salt solution or metal complex solution as rapidly as possible, a vacuum may be applied to the deposition apparatus during deposition or the apparatus may be subjected to ultrasound treatment.

The deposition rate is controlled primarily via the temperature and the pH of the solution. The deposition process is followed by a rinsing and/or drying process. The resulting coating system may, as already described, be subjected to a heat treatment.

The present invention is not limited to the described exemplary embodiments, but rather additional combinations and coating systems beyond the coating systems shown in FIGS. 1 and 2 and described are possible in which a metallic layer in a porous layer are deposited on an electrically conductive and/or metallic base coat.

What is claimed is:

1. A method for manufacturing a coated system, comprising:
   providing a ceramic substrate;
   applying an electrically conductive base coat to the ceramic substrate;
   applying a porous overcoat to the base coat; and
   depositing at least one additional layer through pores of the overcoat onto the base coat; wherein
   the at least one additional layer deposits in a plurality of pores of the porous overcoat, the plurality of pores being adjacent to the electrically conductive base coat, and
   the at least one additional layer has a defined thickness, the defined thickness being less than a thickness of the porous overcoat.

2. The method according to claim 1, wherein the depositing step includes the step of electrolytically depositing the at least one additional layer through the pores of the overcoat onto the base coat.

3. The method according to claim 2, further comprising the step of:
   introducing the ceramic substrate with the base coat and the overcoat into an electrolytic bath;
   connecting the base coat as a cathode using terminal contacts, the terminal contacts being provided on the ceramic substrate; and
   using the at least one additional layer as a anode.

4. The method according to claim 1, wherein the depositing step includes the step of depositing the at least one additional layer through the pores of the overcoat onto the base coat by currentless deposition.

5. The method according to claim 4, further comprising the steps of:
   introducing the ceramic substrate with the base coat and the overcoat into a solution of i) metals to be deposited to form the at least one additional layer, and ii) a chemical reducing agent.

6. The method according to claim 5, further comprising the step of:
   controlling a rate of the deposition via at least one of i) a pH of the solution, and ii) a temperature of the solution.

7. The method according to claim 5, wherein the reducing agent is at least one from the group of aldehydes and formaldehyde.

8. The method according to claim 5, wherein the reducing agent is one of hydrazine and alcohol.

9. The method according to claim 1, wherein the depositing step includes the step of depositing at least one metal from the group of Au, Ni, Co, Cu, Ag, Sn and W as the at least one additional layer.

10. The method according to claim 1, further comprising the step of:
    applying at least one of ultrasound and a vacuum during deposition to accelerate a complete penetration of the porous protective coating covering the base coat.

11. The method according to claims 1, further comprising the step of:
    after the depositing step, performing at least one of a rinsing process and a drying process.

12. The method according to claim 1, further comprising the step of:
    after the depositing step, subjecting the coating system to a heat treatment.

13. The method according to claim 12, wherein a temperature of the heat treatment is below a sintering temperature of the ceramic substrate, the heat treatment forming an alloy of metals of the base coat and of the at least one additional layer.

14. The method of claim 1, wherein the at least one additional layer lies with a first side adjacent to the electrically conductive base coat and a second side adjacent to the porous overcoat, the second side being an opposite side to the first side.

* * * * *

UNITED STATES PATENT AND TRADEMARK OFFICE
CERTIFICATE OF CORRECTION

PATENT NO.    : 6,306,457 B1
DATED         : October 23, 2001
INVENTOR(S)   : Schneider et al.

It is certified that error appears in the above-identified patent and that said Letters Patent is hereby corrected as shown below:

<u>Title page, Item [54] and Column 1, lines 1 and 2,</u>
Change the title from "COATED SYSTEM AND METHOD FOR ITS MANUFACTURE AND USE" to -- METHOD OF MANUFACTURING A COATED SYSTEM --

Signed and Sealed this

Twenty-fourth Day of December, 2002

JAMES E. ROGAN
*Director of the United States Patent and Trademark Office*